United States Patent
Zheng et al.

(10) Patent No.: US 6,840,305 B2
(45) Date of Patent: Jan. 11, 2005

(54) COLD CRANKING SIMULATOR HAVING HYBRID HEAT TRANSFER SYSTEM

(75) Inventors: Wanlie Zheng, State College, PA (US); Larry Russell Hayward, Boalsburg, PA (US)

(73) Assignee: Cannon Instrument Company, State College, PA (US)

(*) Notice: Subject to any disclaimer, the term of this patent is extended or adjusted under 35 U.S.C. 154(b) by 60 days.

(21) Appl. No.: 09/826,021

(22) Filed: Apr. 4, 2001

(65) Prior Publication Data

US 2002/0144800 A1 Oct. 10, 2002

(51) Int. Cl.[7] .................................................. F28F 7/02
(52) U.S. Cl. .................... 165/11.1; 165/138; 62/3.2; 62/3.6; 73/54.43; 73/54.42
(58) Field of Search .................... 165/11.1, 80.1, 165/80.2, 80.5, 80.4, 138; 73/54.43, 54.42; 62/3.2, 3.6, 3.7

(56) References Cited

U.S. PATENT DOCUMENTS

| | | | | |
|---|---|---|---|---|
| 1,688,885 A | * | 10/1928 | Spreen | 165/80.5 X |
| 2,074,174 A | | 3/1937 | Goodier | 265/11 |
| 2,280,133 A | * | 4/1942 | Sundbach | 165/80.5 X |
| 2,812,656 A | | 11/1957 | Merrill | 73/60 |
| 2,955,459 A | | 10/1960 | Cihelka et al. | 73/57 |
| 2,988,914 A | | 6/1961 | Jones | 73/54 |
| 3,035,419 A | * | 5/1962 | Wigert | 165/80.5 X |
| 3,074,266 A | | 1/1963 | Sadler et al. | 73/55 |
| 3,234,781 A | | 2/1966 | Bragg | 73/55 |
| 3,307,619 A | * | 3/1967 | Kim | 165/80.5 X |
| 3,350,922 A | | 11/1967 | Kim et al. | 73/60 |
| 3,470,810 A | * | 10/1969 | Buechner | 165/80.5 |
| 3,535,914 A | | 10/1970 | Veith et al. | 73/15.6 |
| 3,559,463 A | | 2/1971 | Tovrog et al. | 73/55 |
| 3,712,117 A | | 1/1973 | Fitzgerald et al. | 73/59 |

(List continued on next page.)

OTHER PUBLICATIONS

"CMRV–3L Cannon® Mini–Rotary Viscometer Instruction & Operation Manual"; 1996 by Cannon Instrument Co.; pp. 1–7 of 68.

CMRV–4000 Cannon® 4000 Series Mini–Rotary Viscometer Instruction & Operation Manual; 1998 by Cannon Instrument Co.; pp. 1–10 of 80.

Primary Examiner—Ljiljana Ciric
(74) Attorney, Agent, or Firm—Drinker Biddle & Reath LLP

(57) ABSTRACT

A heat transfer apparatus for use in measuring a rheological property of a test sample includes a receptacle for receiving the test sample and a heat conveying member in heat transfer relation to the receptacle. The heat conveying member has internal passages extending substantially equidistantly from one another through at least a portion of the heat conveying member to provide for counter-flow circulation of a fluid. The heat transfer apparatus may include heat exchanging elements in heat transfer relation to the receptacle responsive to electric current to transfer heat to or from the receptacle.

17 Claims, 2 Drawing Sheets

U.S. PATENT DOCUMENTS

| | | | |
|---|---|---|---|
| 3,895,513 A | | 7/1975 | Richardson ............ 73/55 |
| 3,935,726 A | | 2/1976 | Heinz ..................... 73/60 |
| 3,935,729 A | * | 2/1976 | McCarthy |
| 3,999,601 A | * | 12/1976 | Spanoudis ............ 165/80.1 |
| 4,027,516 A | | 6/1977 | Ochodnicky et al. ...... 73/57 |
| 4,048,056 A | | 9/1977 | Romovacek ............ 208/41 |
| 4,152,927 A | | 5/1979 | Feng et al. ............. 73/60 |
| 4,161,213 A | * | 7/1979 | Heide et al. ........ 165/80.4 X |
| 4,165,632 A | * | 8/1979 | Weber et al. |
| 4,335,620 A | * | 6/1982 | Adams |
| 4,346,754 A | * | 8/1982 | Imig et al. ......... 165/80.5 X |
| 4,472,963 A | | 9/1984 | Gyer et al. ............. 73/60 |
| 4,502,531 A | * | 3/1985 | Petersen ............ 165/80.1 X |
| 4,544,489 A | | 10/1985 | Campbell et al. ......... 210/709 |
| 4,574,622 A | * | 3/1986 | Hatfield |
| 4,675,720 A | * | 6/1987 | Ikegame et al. ...... 165/80.1 X |
| 4,700,567 A | * | 10/1987 | Frey et al. |
| 4,729,667 A | * | 3/1988 | Blangetti et al. ...... 165/11.1 X |
| 4,959,995 A | | 10/1990 | Deysarker et al. ......... 73/54 |
| 5,203,401 A | * | 4/1993 | Hamburgen et al. ... 165/80.5 X |
| 5,331,844 A | | 7/1994 | Noren ..................... 73/54 |
| 5,423,302 A | | 6/1995 | Glassey ................. 123/446 |
| 5,520,042 A | | 5/1996 | Garritano et al. ........ 73/54.02 |
| 5,714,685 A | * | 2/1998 | Hobro et al. ........ 165/11.1 X |
| 5,841,634 A | * | 11/1998 | Visser ............... 165/80.5 X |
| 5,852,230 A | | 12/1998 | Selby et al. ............. 73/54.35 |
| 6,146,895 A | * | 11/2000 | Green et al. |
| 6,330,153 B1 | * | 12/2001 | Ketonen et al. ...... 165/80.3 X |

* cited by examiner

COLD CRANKING SIMULATOR HAVING HYBRID HEAT TRANSFER SYSTEM

FIELD OF THE INVENTION

The present invention relates to a cold cranking simulator for rheological testing of a liquid sample and, more particularly, to a cold cranking simulator having a hybrid system for transferring heat to or from a liquid sample.

BACKGROUND OF THE INVENTION

Engine oil protects the moving parts of an engine by providing a lubricating coating to reduce friction generated by the moving parts. The ability of the engine oil to properly lubricate the moving parts of the engine is largely dependent on rheological properties of the oil, in particular the viscosity of the engine oil. In general terms, viscosity is a measure of resistance of a fluid to flow. In an engine, the oil fills the narrow spaces between the parts and clings to both moving and non-moving parts. The tendency of the oil to remain in contact with both the moving and non-moving parts creates internal frictional forces within the oil. These internal forces must be overcome before relative movement between the parts can occur. The internal forces within the oil will vary in proportion to the viscosity of the oil and will increase with increasing viscosity. Additionally, for a given blend of engine lubricating oil, the viscosity will not remain constant, but will vary as a function of temperature, becoming much more viscous in cold temperatures. The resulting increased frictional forces associated with the increased viscosity renders engine operation or "cranking" more difficult in low temperature conditions.

Known rheological test devices include devices known as "cold-cranking simulators" which are used to test engine oils at low temperatures under simulated engine starting conditions for compliance with the Society of Automotive Engineers (SAE) Standard J300. The testing of oils using these devices is governed by the American Society for Testing and Materials (ASTM) D5293 "Standard Test Method for Apparent Viscosity of Engine Oils Between −5 and −35° C. Using the Cold-Cranking Simulator." A cold cranking simulator measures the apparent viscosity of an engine oil by measuring the resistance to rotation imposed on a rotor by a sample of oil delivered into a narrow annular space between the rotor and a non-moving stator. The cold cranking simulator therefore differs in operation from devices such as capillary viscometers which measure flow rate of a fixed volume of a fluid through an orifice. The results of testing on a sample of engine oil using a cold cranking simulator are called the "cranking viscosity" of the engine oil.

An example of a cold cranking simulator is shown in U.S. Pat. No. 4,472,963 to Gyer. A sample of oil is introduced into a narrow annular space between a rotatably supported rotor and fixed stator. A probe is located within the stator to monitor the temperature of the stator. Methanol from a cold bath is circulated through coolant conduits in the stator to cool the stator. The methanol in the cold bath is maintained at a constant predetermined temperature differential below the test temperature. The methanol is introduced into the stator through a valve which is periodically opened and closed to control flow of coolant. A control system is responsive to the temperature from the stator probe to adjust the on-to-off time of the valve thereby controlling the amount of methanol delivered to the stator. Methanol is also heated to just below boiling in a separate hot bath for circulation through the coolant passages of the stator between tests to facilitate removal of the tested sample. The heated methanol facilitates the removal of the tested sample by reducing the viscosity of the oil thereby reducing the resistance of the oil to flow.

Methanol is a flammable and highly toxic substance. The storage and handling of the methanol in the baths and in the circulating system of the cold cranking simulator of the '963 patent therefore represents a threat to health and safety. The safety concerns raised by the use of methanol in the '963 patent are further increased by the use of the hot bath in which the flammable methanol is heated to close to its boiling point. Furthermore, heat transfer provided by the circulating methanol is inefficient and limits the rate at which the stator is cooled. The inefficiencies inherent in the circulating methanol also limit the responsiveness of the system to changing heat transfer requirements resulting in imprecision in the temperature control provided by the system.

The temperature control provided by the '963 system is further limited as a result of temperature variations necessarily created along the flow path of the circulating fluid. The circulation of a coolant fluid through a heat conveying member for the purposes of heat transfer between the member and the fluid inherently results in a variation in temperature along the path of the circulating coolant fluid as heat is added or removed from the coolant medium. Circulating systems of prior art cold cranking simulators, such as the simulator of U.S. Pat. No. 4,472,963 to Gyer, direct coolant fluid between an inlet located at a first side of the stator to an outlet located on an opposite side of the stator. The coolant fluid is directed in the conduits of the '963 simulator in a unidirectional circulation of the coolant fluid in which, at any given location of the stator, coolant is being directed in a single direction. As chilled methanol is directed about the stator, heat added to the methanol from the stator will raise the temperature of the methanol between the inlet and the outlet. As a result, temperature gradients will be created across the stator between the coolant inlet and outlet.

What is needed is a heat transfer system for varying the temperature of a test sample in a cold cranking simulator which provides for increased precision and uniformity in sample temperature control by increased responsiveness to changing heat transfer requirements and limitation of temperature gradients across the test sample.

SUMMARY OF THE INVENTION

According to the present invention, there is provided a heat transfer apparatus for use in measuring a rheological property of a test sample. The apparatus includes a receptacle for receiving the test sample and a heat conveying member in heat transfer relation to the receptacle. The heat conveying member has internal passages which extend substantially equidistant from one another through at least a portion of the heat conveying member to provide for a counter-flowing circulation of a fluid.

According to an embodiment of the invention the heat conveying member includes heat sinks interconnected to form an assembly of heat sinks. Tubular members extend between adjoining heat sinks to connect internal passages of adjoining heat sinks.

According to an embodiment of the invention, there is provided a cold cranking simulator. The cold cranking simulator includes a receptacle for receiving a sample of oil. The cold cranking simulator further includes a hybrid heat transfer system having at least one heat exchanging element in heat transfer relation to the receptacle and responsive to electric current to transfer heat to or from the receptacle. The cold cranking simulator further includes a heat conveying member in heat transfer relation to the heat exchanging element to provide for transfer of heat to or from the heat exchanging element. The heat conveying member includes internal passages which extend substantially equidistant from one another through at least a portion of the heat conveying member to provide for a counter-flowing circulation of a fluid.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
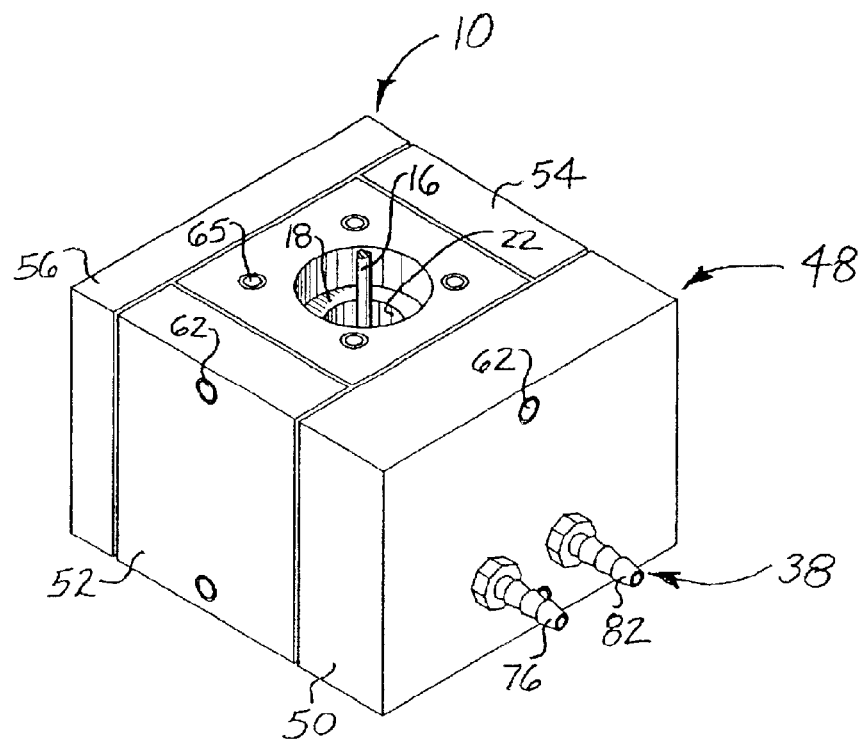
FIG. 1 is a perspective view of the test cell of a cold cranking simulator according to the present invention.

Referring to the drawings where like numerals identify like elements, there is shown a test cell 10 of a cold cranking simulator according to the present invention for use in rheological testing of a sample of oil at low temperatures under governing standards identified in ASTM D 5293. The cold cranking simulator is used to simulate automobile engine starting conditions in cold temperatures and determines an apparent viscosity, known as the "cranking" viscosity, by measuring the resistance to rotation imposed on a rotor by a sample of oil delivered into a narrow annular space between the rotor and a non-moving stator. In the manner to be described, the test cell 10 transfers heat to and from the test cell and provides for uniform test sample temperature and precision control over temperature within 0.01° C. for test temperatures as low as −40° C. The precision of the temperature control system is facilitated by a heat transfer system capable of rapidly responding to changing heat transfer requirements. Furthermore, the test cell utilizes a highly compact arrangement of parts leading to space saving efficiencies and economy of materials.

As seen in FIGS. 1–4, the cold cranking simulator includes a cylindrical rotor 14 which is supported for rotation by shaft 16. The rotor 14 is concentrically located within the opening of a hollow cylindrical stator 18. The outer surface 20 of the rotor 14 and the inner surface 22 of the stator 18 are closely toleranced and precisely machined such that a narrow annular space 24 may be maintained between the rotor 14 and the stator 18 by the cold cranking simulator as the rotor 14 is rotated within the stator 18. The annular space 24 simulates the spaces between closely fitting moving parts of an engine to provide for measurement of the cranking viscosity of the oil sample under low temperatures.

Figure 4:
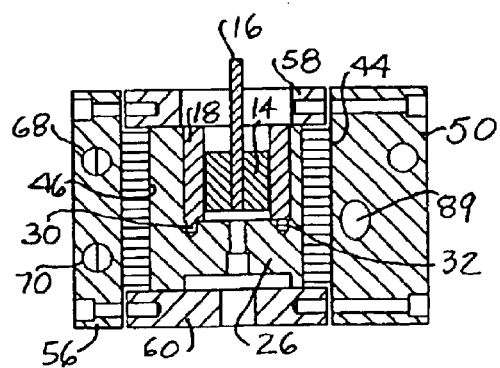
FIG. 4 is a sectional view taken along the lines 4—4 of FIG. 2.

The test cell 10 includes a block 26 preferably made of a highly thermally conductive metal such as copper to facilitate heat transfer through the block 26. The block 26 includes a central bore 28 extending from an upper surface of the block defining a cavity which serves as a receptacle for the test cell 10 in which the sample of oil to be tested is received. As seen in FIG. 4, the stator 18 is positioned within the cavity of block 26 and aligned to the block by a pin 30 extending from the stator 18. The pin 30 in the stator 18 is received in a hole 32 formed in a surface of the block 26 at the terminal end of the central bore 28. The block 26 also includes a counterbored passage 34 extending from a lower surface of the block and communicating with the central bore 28. A sample of oil to be tested is introduced into the annular space 24 between the rotor 14 and stator 18 through the counterbored passage 34 and is cooled to a test temperature by the temperature control system of test cell 10. The viscosity of the oil sample is then tested by the cold cranking simulator in the well known manner by measuring the resistance to rotation of the rotor 14 that is imposed on the rotor by the oil sample located in the annular space 24.

Figure 3:
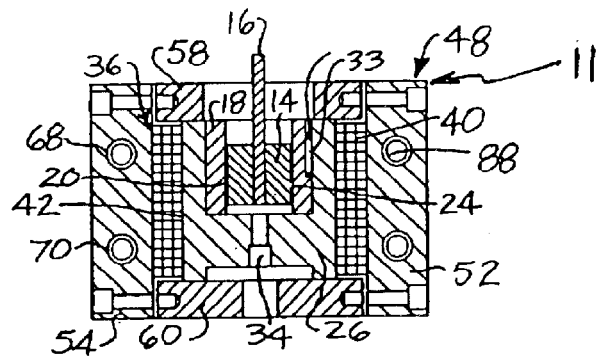
FIG. 3 is a sectional view taken along the lines 3—3 of FIG. 2.

As seen in FIG. 3, the test cell 10 includes a temperature probe 33 which is inserted in a notch formed in the outer surface 35 of the stator 18 such that the probe confronts the block 26 at the interface between the stator 18 and the block 26. This positions the probe 33 in temperature monitoring proximity to the stator 18 in which the sample of oil will be received. The probe 33 is electrically connected by wire, shown extending from the stator 18, to a control system for test cell 10 for transmission of an electrical signal representing the interface temperature as measured by the probe 33. As will be described in greater detail, the control system of test cell 10 is responsive to the reported temperature from probe 33 to adjust the heat transfer provided by test cell 10, thereby controlling sample temperature. Locating the temperature probe 33 at the interface between the stator 18 and the block 26 rather than fully within the stator 18 or the block 26 enhances the responsiveness of the test cell 10 to changes in thermal load thereby facilitating precise temperature control.

The test cell 10 of the cold cranking simulator includes a hybrid heat transfer system 11 in which heat transfer from the block 26 to cool the test sample is provided by a first heat transfer system 36. The heat transfer provided by the first heat transfer system 36 is adjustable to provide for control over the temperature of the sample. The hybrid heat transfer system of the test cell 10 further includes a second heat transfer system 38 which functions to convey the heat which has been removed from block 26 by the controllable first heat transfer system 36.

The first heat transfer system 36 includes thermoelectric modules 40 each of which is positioned to extend along one of four planar side surfaces 42 of the block 26. The thermoelectric modules 40 use a principal known as the "Peltier effect" in which electrical current is directed through the modules by the first heat transfer system 36 to establish opposite hot and cold surfaces of the modules 40. In the normal operating mode of the first heat transfer system in which the modules 40 are used to cool the test sample, the current is directed through the modules 40 such that the hot surfaces of the modules 40 established by the first heat transfer system 36 are surfaces 44 on the outermost sides of the modules.

The effective heat transfer provided by the Peltier effect of the thermoelectric modules 40 and the intimate proximity of the modules to the block 26 provides for rapid transfer of heat from the block 26 to the hot sides 44 of the modules 40 and rapid cooling of the test sample in block 26. Transferring heat from the block 26 by thermoelectric modules adjacent the block 26 also provides for increased responsiveness of the cold cranking simulator to changes in required heat transfer from the block 26 in the following manner. In response to reported temperature by probe 33, the rate of heat transfer from block 26 may be instantly varied through control over the current which is delivered to the modules 40 by the first heat transfer system 36. Variation in current delivered to the modules 40 may be accomplished alternatively by variation in on-to-off time of a duty cycle of a set current or by variation in the amperage of the current. Furthermore, because equal current may be delivered to each of the modules 40, the first heat transfer system provides for a more balanced heat transfer from the block 26 over methanol circulating systems of the prior art. The increased responsiveness and uniformity of heat transfer from the test sample greatly facilitates precision in the control of sample temperature by test cell 10.

The Peltier effect of the modules 40 provides for an alternate mode of operation of the modules 40 to that described above. By reversing the direction of the current directed through the modules by the first heat transfer system 36, the hot and cold surfaces of the modules will be reversed from that described above. In this alternate mode of operation, the hot surfaces of the modules 40 will be surfaces 46 located on the innermost sides of the modules such that heat is directed into the block 26 rather than removed. The alternate mode of operation provides for rapid heating of the block 26. This is useful for removal of a tested sample because the heating of the sample reduces the viscosity of the oil thereby decreasing the resistance of the oil to flow from the cavity of the test cell 10. The rapid heating and removal of a tested sample from the test cell 10 by reversal of current provided to the modules 40 eliminates the need for introducing heat from a separate source such as the separate hot methanol baths of prior art devices.

It should be understood by those skilled in the art that the thermoelectric modules 40 of the foregoing description are not limited to single-stage modules. Depending on the desired test temperature and the cooling capability of available single-stage modules, it may be preferable that the thermoelectric modules 40 comprise multi-stage modules. A multi-stage module, per se well known in the art, has typical application where larger temperature differentials are desired across the thermoelectric module. In a multi-stage module, separate stages, each constituting a separately charged thermoelectric layer, are stacked one on top of another to form the thermoelectric module. Where a multi-stage module is used for the thermoelectric module 40, reference herein to the "hot" and "cold" side of the module 40 should be understood to refer to either the innermost or outermost surface of the stacked layers depending on which of the alternate heating or cooling modes of operation is applicable.

The second heat transfer system 38 of the test cell 10 uses a circulating fluid to convey heat away from the test cell 10. However, in contrast to prior art simulators using circulating methanol, heat transfer with the sample for temperature control is provided by the thermoelectric modules 40 instead of by the circulating fluid. The circulating fluid of the second heat transfer system 38 of test cell 10 functions merely to convey heat away from the hot sides of the modules 40. As a result, methanol is not required as the circulating fluid. A mixture of water and ethylene glycol, a commonly used engine coolant, provides a suitable circulating fluid for test temperatures down to −40° C. Furthermore, depending on desired test temperature and required heat loads, water alone may be sufficient. The elimination of methanol, a flammable and highly toxic material, enhances operator health and safety.

The incorporation of thermoelectric modules 40 in test cell 10 for controlled heat transfer with the sample simplifies required control of the circulating fluid in contrast to prior art circulating methanol systems. For the simulator disclosed in U.S. Pat. No. 4,472,963 to Gyer, for example, it was necessary that cooling baths be provided to chill the methanol to a set number of degrees below the desired test temperature. Changing test temperatures required corresponding changes in the inlet temperature of the methanol. For test cell 10, circulation of a water/glycol ethylene mixture from a mechanical chiller at approximately +5° C. provides for sufficient conveyance of heat from the modules 40 of test cell 10 for any test temperature down to −40° C. However, the invention is not limited to circulation of a water/ethylene glycol mixture from a mechanical chiller. Depending on the desired test temperature and required heat load, circulation of fluid from an air-water heat exchanger or circulation of ordinary tap water may be sufficient.

Figure 2:
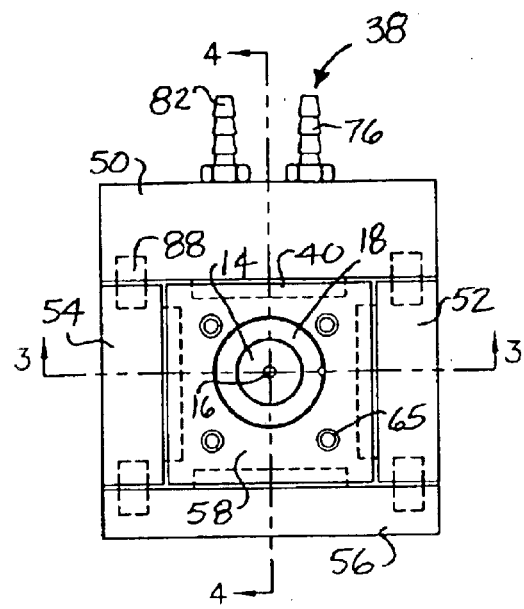
FIG. 2 is a top plan view of the test cell of FIG. 1 (rotated 90°)

The second heat transfer system 38 includes an assembly 48 of heat sinks which serves as a heat conveying member for removal of heat from the hot sides of the modules 40. The heat sinks are made from a thermally conductive material such as aluminum or copper, for example. Each of the heat sinks of the assembly 48 extends adjacent to the outer surface 44 of one of the modules 40 of the first heat transfer system 36 such that the heat sinks collectively surround the modules 40 and block 26. The assembly 48 of heat sinks includes a rear heat sink 50, opposite side heat sinks 52, 54 and front heat sink 56. As seen in FIGS. 1 and 2, the side heat sinks 52, 54 extend between end portions of the rear heat sink 50 and the front heat sink 56 such that the ends of the side heat sinks confront the end portions of the front and rear heat sinks. The confronting relationship between the side heat sinks 52, 54 and the front and rear heat sinks 56, 50 results in a highly compact and generally square assembly of heat sinks. The adjoining relationship between the ends of the side heat sinks and the end portions of the front and rear heat sinks facilitates insulation of block 26 which is surrounded by the assembly 48 such that the use of additional insulating material such polyurethane is eliminated. An equally feasible arrangement of heat sinks in which the side heat sinks extend such that the ends of the front and rear heat sinks confront end portions of the side heat sinks would also provide for a compact assembly eliminating the need for additional insulating material.

The test cell 10 includes a top cover 58 extending between the heat sinks, above the block 26 and the modules 40 of the first heat transfer system 36. The test cell further includes a bottom cover 60 extending between the heat sinks, below the block 26 and the modules 40. The top and bottom covers 58, 60 are secured to the front, rear and side heat sinks by bolts 62. The bolts extend through the countersunk openings in the front heat sink 56, the rear heat sink 50, and the side heat sinks 52, 54 to engage tapped holes in the top and bottom covers 58, 60. The interfit of the top and bottom covers 58, 60 between the heat sinks of the assembly 48 provides for an extremely compact and generally cube shaped enclosure surrounding the block 26 and the modules 40 of the first heat transfer system 36. The compact cube-shaped enclosure provides sufficient insulation for precision controlled test temperatures as low as −40° C. without the need for supplemental insulating material.

The assembly 48 of heat sinks define internal passages which are interconnected to form series of passages through which the fluid of the second heat transfer system 38 may be circulated. The system of passages includes transversely disposed upper passages 68 and lower passages 70 in each of the side heat sinks 52, 54 and front heat sink 56 which, when aligned, form portions of first and second series 72, 74 of passages. As seen in the Figures, the upper and lower passages 68, 70 extend through the assembly 48 of heat sinks separated from one another by a distance which remains substantially equal. The equidistant spacing of the passages 68, 70 provides for a counter-flowing circulation of separated portions of fluid in the passages in the manner to be described in greater detail. Although the equidistant relationship of the preferred passages involves a separation between the upper and lower passages, it is conceivable that the passages could comprise concentric cylindrical passages such that the equidistant spacing between the passages is zero. The rear heat sink 50 includes an arrangement of passages which provides for division of the fluid into separate portions for counter-flowing channeling of the separated portions through the first and second series 72, 74 of passages.

Figure 5:
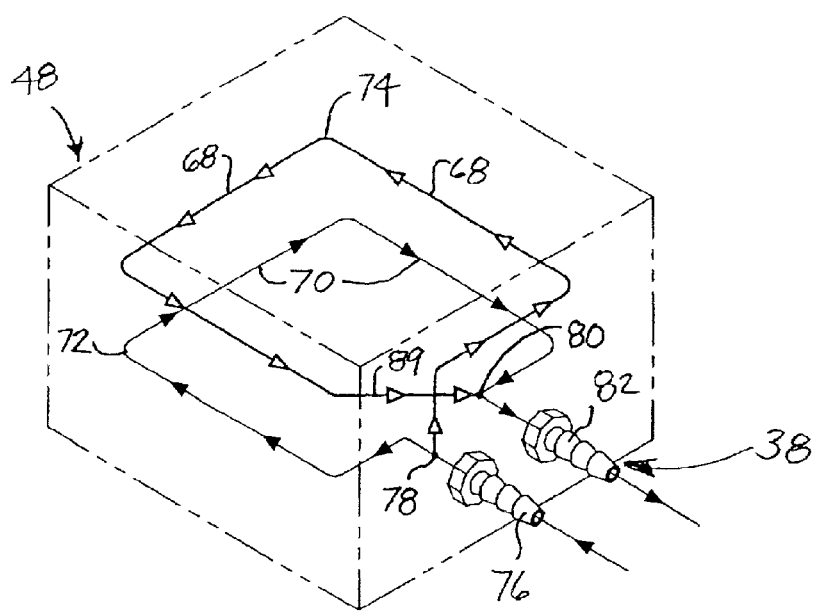
FIG. 5 is a schematic illustration of the counter-flowing series of passages provided in the test cell of FIG. 1.

As shown schematically in FIG. 5 fluid is introduced into the test cell through inlet 76, preferably from a mechanical chiller at a constant temperature +5° C. The rear heat sink 50 includes a passage splitter 78 adjacent inlet 76 which forms separate passages thus dividing the fluid introduced into the cell via inlet 76 into first and second portions. The first portion of the fluid is directed around the test cell 10 in the first series 72 of passages in a clockwise direction while the second portion of the fluid is directed in the second series 74 of passages in a counterclockwise direction. As shown, the passages of the respective series of passages are preferably located above and below one another with respect to the heat sink assembly. The rear heat sink 50 further includes a passage union 80 adjacent an outlet 82 which joins the separate passages of the first and second series 72, 74 of passages into a single passage.

The rear heat sink 50 provides for the division and reunion of the fluid necessary for the counter-flowing circulation of the second heat transfer system in the following manner. As discussed above, the fluid is divided into first and second portions by passage splitter 78. The first portion is channeled in a lower part of rear heat sink 50 to side heat sink 52. The first portion is then channeled through the lower passages 70 of side heat sink 52, front heat sink 56 and side heat sink 54. The first portion is then channeled in a lower part of rear heat sink 50 to the passage union 80.

The second fluid portion created by the passage splitter 78 is initially channeled upwardly from the splitter in an upper part of rear heat sink 50 to side heat sink 54. The second portion is then channeled through the upper passages 68 in a counterclockwise direction through side heat sink 54, front heat sink 56 and side heat sink 52. An angling passage 89 in rear heat sink 50 channels the second portion of fluid to the passage union 80 for merging of the second portion with the first portion. As shown, the angling passage 89 of the second series 74 of passages is located inwardly from the passages of the first series 72 with respect to the rear heat sink 50. The united flow is then discharged from the test cell 10 through outlet 82, for return to the mechanical chiller for example.

In the normal operating mode of the hybrid heat transfer system in which the circulating water mixture is conveying heat away from the thermoelectric modules 40, the temperature of the first portion of the water mixture will be increased as the fluid is channeled about the test cell 10 in a clockwise direction. Similarly, the temperature of the second portion of the fluid will be increased as the fluid is channeled about the test cell in a counter-clockwise direction. As a result, the average temperature of the two portions of the fluid will be substantially equalized regardless of location around the test cell 10. In this manner, temperature gradients which would otherwise be formed across the test cell 10 are minimized by the counter-flowing circulation system of test cell 10. The reduction of temperature gradients across the test cell 10 facilitates uniformity in the sample temperature.

It is most preferable that the inlet 76 and outlet 82 be located closely to one another as seen in FIGS. 1 and 2. In this manner, the length of transversely disposed passages located above and below one another in the rear heat sink 50 will be maximized thereby facilitating the gradient-reducing function of the divided counter-flowing system of the second heat transfer system 38.

The internal passages in the assembly 48 of heat sinks are arranged such that, at each of the interfaces between adjoining heat sinks, each of the internal passages of one heat sink confronts an internal passage of the adjoining heat sink. The second heat transfer system 38 preferably includes tubular members 88 each of which extends between confronting passages of adjoining heat sinks. The tubular members 88 provide passage segments serving to interconnect the otherwise separate passages of the first and second flow pathways 72, 74 of the second heat transfer system 38. A suitable gasket material, such as silicone, can be used to seal the separate heat sinks and connecting tubular members 88. The use of a single inlet 76 and outlet 82 for the test cell 10 and connecting tubular members 88 to link confronting passages in the heat sinks provides compactness in comparison to the use of separate inlets and outlets for each heat sink connected together by flexible tubing externally of the assembly.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather should be construed in breadth and scope in accordance with the recitation of the appended claims.

What is claimed is:

1. A heat transfer apparatus for use in measuring a rheological property of a test sample, the heat transfer apparatus comprising:
   a receptacle for receiving the test sample; and
   a heat conveying member disposed in heat transfer relation to the receptacle, the receptacle located within an interior defined by the heat conveying member such that the receptacle is substantially surrounded by the heat conveying member, the heat conveying member including
      at least first and second internal passages spaced apart from one another through at least a portion of the heat conveying member, each of the first and second internal passages having first and second ends,
      an inlet,
      an outlet,
      a passage splitter connected to the inlet and the first ends of the first and second internal passages for dividing a flow of a fluid from the inlet between the first and second internal passages, and
      a passage union connected to the outlet and the second ends of the first and second internal passages,
      each of the first and second internal passages defining a substantial complete loop around the interior of the conveying member and the receptacle therein,
      the passage splitter and the first and second internal passages arranged for counter-flow circulation in which a flow of fluid is respectively directed in the first and second internal passages through the heat conveying member in clockwise and counterclockwise directions.

2. The heat transfer apparatus according to claim 1 wherein the heat conveying member is formed from a plurality of heat sinks interconnected to one another, the inlet and outlet of the heat conveying member being located adjacent each other on one of the plurality of heat sinks.

3. The heat transfer apparatus according to claim 2 wherein the plurality of heat sinks interconnect so as to define a substantially square housing for the receptacle.

4. The heat transfer apparatus according to claim 1 wherein the heat transfer apparatus further comprises at least one heat exchanging element disposed in heat transfer relation to the receptacle to transfer heat to and from the receptacle, the heat exchanging element being in heat transfer relation to the heat conveying member for transferring heat to or from the heat conveying member.

5. The heat transfer apparatus according to claim 4 wherein the heat exchanging element comprises a thermoelectric module, the module adapted to receive electric current to transfer heat through the module from a first side of the module to an opposite second side of the module.

6. The heat transfer apparatus according to claim 5 wherein the thermoelectric module comprises a multi-stage thermoelectric module.

7. A heat transfer apparatus for use in measuring a rheological property of a test sample, the heat transfer apparatus comprising:
   a receptacle for receiving the test sample;
   a heat conveying member disposed in heat transfer relation to the receptacle, the heat conveying formed from a plurality of heat sinks interconnected to one another so as to surround at least a portion of the receptacle, the heat conveying member including
      at least first and second internal passages spaced apart from one other through at least a portion of the heat conveying member, each of the first and second internal passages having first and second ends,
      an inlet,
      an outlet,
      a passage splitter connected to the inlet and the first ends of the first and second internal passages for dividing flow through the inlet into the first and second internal passages, and
      a passage union connected to the outlet and the second ends of the first and second internal passages, the passages formed so as to provide for counter-flow circulation of a fluid through the heat conveying member,
   the first and second internal passages extending through at least a portion of each of the plurality of heat sinks; and
   a plurality of connectors each extending between adjoining heat sinks and connecting one of the first and second internal passages of one of the adjoining heat sinks with a corresponding one of the first and second internal passages in the other of the adjoining heat sinks for permitting fluid to pass through the internal passages from one heat sink to the other.

8. A cold cranking simulator comprising:
   a receptacle for receiving a sample;
   at least one heat exchanging element disposed in heat transfer relation the receptacle, the heat exchanging element responsive to electric current to transfer heat to or from the receptacle; and
   a heat conveying member in heat transfer relation to the heat exchanging element for transferring heat to or from the heat exchanging element, the receptacle and the at least one heat exchanging element located within an interior defined by the heat conveying member such that the receptacle and the at least one heat exchanging element are substantially surrounded by the heat conveying member, the heat conveying member having first and second internal passages spaced apart from one another through at least a portion of the heat conveying member, the first and second internal passages having first and second ends,
      an inlet,
      an outlet,
      a passage splitter connected to the inlet and the first ends of the first and second internal passages for dividing a flow of a fluid from the inlet between the first and second internal passages, and
      a passage union connected to the outlet and the second ends of the first and second internal passages,
      each of the first and second internal passages extending in a substantially complete loop around the interior of the heat conveying member and the receptacle therein, the passage splitter and the first and second internal passages arranged for counter-flow circulation in which a fluid is respectively directed in the first and second internal passages through the heat conveying member in clockwise and counterclockwise directions.

9. The cold cranking simulator according to claim 8 wherein the heat conveying member is formed from a plurality of heat sinks interconnected to one another, the inlet and outlet of the heat conveying member being located adjacent each other on one of the plurality of heat sinks.

10. The cold cranking simulator according to claim 8 further comprising a temperature control system having a temperature probe for generating a signal representing a temperature monitored by the probe, the control system in electrical communication with the heat exchanging element and responsive to the signal for controlling the current supplied to the heat exchanging element.

11. A cold cranking simulator comprising:
   a receptacle for receiving a sample;
   at least one heat exchanging element disposed in heat transfer relation to the receptacle, the heat exchanging element adapted to receive electric current for transferring heat to or from the receptacle by means of the heat exchanging element;
   a heat conveying member in heat transfer relation to the heat exchanging element for transferring heat to or from the heat exchanging element, the heat conveying member having first and second internal passages spaced apart from one another through at least a portion of the heat conveying member, the first and second internal passages having first and second ends,
      an inlet,
      an outlet,
      a passage splitter connected to the inlet and the first ends of the first and second internal passages for dividing flow through the inlet into the first an second internal passages, and
      a passage union connected to the outlet and the second ends of the first and second internal passages;
      the passages formed so as to provide for counter-flow circulation of a fluid, the first and second internal passages extending through at least a portion of each of the plurality of heat sinks; and a plurality of connectors each extending between adjoining heat sinks and connecting one of the first and second internal passages of one of the adjoining heat sinks with a corresponding one of the first and second internal passages in the other of the adjoining heat sinks for permitting fluid to pass through the first and second internal passages from one heat sink to the other.

12. A heat transfer apparatus for use in controlling the temperature of a sample container, the heat transfer apparatus comprising a heat transfer housing having a wall and a bottom, the wall having an inside surface defining a cavity within the housing, the wall including at least one electrical heat transfer device for controlling heat transfer from the inside surface of the wall, the wall having an inlet port, an outlet port and an internal cooling circuit that extends from the inlet port to the outlet port, the cooling circuit including first and second channels connected to the inlet port and the outlet port, each of the first and second channels defining a substantially complete loop about the cavity of the housing, the first and second channels arranged for counter-flowing circulation in which the flow through the housing in the first and second channels is in opposite directions.

13. A heat transfer apparatus according to claim 12 wherein the wall is made up of multiple sections, each wall section adapted to removably engage with two adjacent wall sections the inlet port and the outlet port located adjacent each other on one of the multiple wall sections.

14. A heat transfer apparatus according to 13 wherein the inlet and outlet ports are formed in one of the multiple wall sections and wherein the first and second channels extend through each of the other ones of the multiple wall sections.

15. A heat transfer apparatus for use in controlling the temperature of a sample container, the heat transfer apparatus comprising
  a heat transfer housing having four wall sections and a bottom, the wall sections having an inside surface defining a cavity within the housing and an outside surface;
  at least two thermal electrical units mounted in two of the wall section in heat transfer relationship with the inside surface, each of the thermal electrical units responsive to electric current for controlling heat transfer from the inside surface of the wall;
  an inlet port formed extending from the outside surface of one wall section into the wall;
  an outlet port formed extending from the outside surface of one wall section into the wall;
  an internal cooling circuit extending between the inlet port and the outlet port, the cooling circuit including first and second channels, the first and second channels each having a first end connected to the inlet port, and a second end connected to the outlet port, the first channel extending through the wall sections from the inlet port to the outlet port in a first direction, the second channel extending through the wall sections from the inlet port to the outlet port in a substantially opposite direction from the first channel such that in operation flow though the first and second channels are in opposite directions.

16. A heat transfer apparatus according to claim 15 wherein the first ends of the first and second channel are connected to the inlet port through a splitter, and wherein the splitter is formed in the same wall section as the inlet port; and wherein the second ends of the first and second channels are connected to the outlet port through a splitter, and wherein the splitter is formed in the same wall section as the outlet port.

17. A heat transfer apparatus according to claim 15 wherein the inlet port and the outlet port are formed in the same wall section.

* * * * *